US00RE36849E

United States Patent [19]

Schad et al.

[11] E Patent Number: Re. 36,849

[45] Reissued Date of Patent: Sep. 5, 2000

[54] ANISOTROPIC COMPOUNDS AND LIQUID CRYSTAL MIXTURES THEREWITH

[75] Inventors: Hans P. Schad, Rieden; Stephen M. Kelly, Kaiseraugst, both of Switzerland; Eike Poetsch, Muhltal, Germany; Reinhard Hittich, Modautal, Germany; Georg Weber, Erzhausen, Germany

[73] Assignee: Merck Patent GmbH, Darmstadt, Germany

[21] Appl. No.: 08/041,349

[22] Filed: Apr. 1, 1993

Related U.S. Patent Documents

Reissue of:

[64] Patent No.: 4,710,315
Issued: Dec. 1, 1987
Appl. No.: 08/815,708
Filed: Apr. 13, 1985

U.S. Applications:

[63] Continuation of application No. 07/444,251, Dec. 1, 1989, abandoned.

[30] Foreign Application Priority Data

Apr. 16, 1984 [CH] Switzerland ..... 1900/84
Apr. 13, 1985 [WO] WIPO ..... PCT/EP85/00163

[51] Int. Cl.[7] ..... C09K 19/30; C07C 121/00; C07C 121/75; C07C 121/60

[52] U.S. Cl. ..... 252/299.63; 252/299.6; 252/299.5; 252/299.66; 560/138; 560/141; 558/414; 558/419; 558/423; 558/424; 558/425; 568/631; 568/642; 568/643; 568/645; 568/647; 568/660; 568/661; 570/129; 570/182; 570/184

[58] Field of Search ..... 252/299.6, 299.63, 252/299.66, 299.5; 560/138, 141; 558/414, 419, 423, 424, 425; 568/631, 642, 643, 645, 647, 660, 661; 570/129, 182, 184

[56] References Cited

U.S. PATENT DOCUMENTS

| | | | |
|---|---|---|---|
| 3,058,953 | 10/1962 | McMaster . | |
| 4,035,056 | 7/1977 | Coates et al. | 252/299.65 |
| 4,108,906 | 8/1978 | Anderson . | |
| 4,257,078 | 3/1981 | Carr et al. | 252/299.62 |
| 4,261,651 | 4/1981 | Gray et al. | 252/299.63 |
| 4,368,135 | 1/1983 | Osman | 252/299.63 |
| 4,400,293 | 8/1983 | Römer et al. | 252/299.63 |
| 4,424,371 | 1/1984 | Hsu | 252/299.61 |
| 4,455,261 | 6/1984 | Sasaki et al. | 252/299.63 |
| 4,455,443 | 6/1984 | Takatsu et al. | 252/299.63 |
| 4,502,974 | 3/1985 | Suginori et al. | 252/299.63 |
| 4,510,069 | 4/1985 | Eipenschink | 252/299.63 |
| 4,512,636 | 4/1985 | Andrews et al. | 252/299.61 |
| 4,551,280 | 11/1985 | Sasaki et al. | 252/299.63 |
| 4,556,745 | 12/1985 | Carr et al. | 252/299.62 |
| 4,564,694 | 1/1986 | Hirai et al. | 252/299.6 |
| 4,565,425 | 1/1986 | Petrzilka et al. | 252/299.63 |
| 4,583,826 | 4/1986 | Petrzilka et al. | 252/299.61 |
| 4,602,851 | 7/1986 | Jenner et al. | 252/299.63 |
| 4,606,845 | 8/1986 | Römer et al. | 252/299.63 |
| 4,621,901 | 11/1986 | Petrzilka et al. | 252/299.63 |
| 4,630,896 | 12/1986 | Petrzilka et al. | 252/299.63 |
| 4,637,897 | 1/1987 | Kelly | 252/299.63 |
| 4,652,089 | 3/1987 | Oesterhelt et al. | 252/299.63 |
| 4,659,502 | 4/1987 | Fearon et al. | 252/299.66 |
| 4,664,840 | 5/1987 | Osman | 252/299.63 |
| 4,709,030 | 11/1987 | Petrzilka et al. | 252/299.63 |
| 4,724,097 | 2/1988 | Römer et al. | 252/299.63 |
| 4,770,503 | 9/1988 | Buchecker | 252/299.66 |
| 4,797,228 | 1/1989 | Goto et al. | 252/299.63 |
| 4,820,443 | 4/1989 | Goto et al. | 252/299.63 |
| 4,877,547 | 10/1989 | Weber et al. | 252/299.66 |
| 4,917,819 | 4/1990 | Goto et al. | 252/299.63 |
| 4,925,590 | 5/1990 | Reiffenrath et al. | 252/299.66 |
| 4,985,583 | 1/1991 | Eidenschink et al. | 252/299.63 |

FOREIGN PATENT DOCUMENTS

| | | |
|---|---|---|
| 019665 | 12/1980 | European Pat. Off. . |
| 023728 | 2/1981 | European Pat. Off. . |
| 028305 | 5/1981 | European Pat. Off. . |
| 084194 | 7/1983 | European Pat. Off. . |
| 107116 | 5/1984 | European Pat. Off. . |
| 129177 | 12/1984 | European Pat. Off. . |
| 149208 | 7/1985 | European Pat. Off. . |
| 168683 | 1/1986 | European Pat. Off. . |
| 2404999 | 8/1975 | Germany . |
| 2635099 | 2/1978 | Germany . |
| 2635100 | 2/1978 | Germany . |
| 2709032 | 9/1978 | Germany . |
| 2731214 | 2/1979 | Germany . |
| 3317921A1 | 12/1983 | Germany . |
| 3317597 | 11/1984 | Germany . |
| 3410734 | 10/1985 | Germany . |
| 57-38760 | 2/1982 | Japan . |
| 57-54137 | 2/1982 | Japan . |
| 57-50933 | 3/1982 | Japan . |
| 57-59851 | 4/1982 | Japan . |
| 57-154158 | 9/1982 | Japan . |
| 58-13544 | 1/1983 | Japan . |
| 58-49355 | 3/1983 | Japan . |
| 58-118543 | 7/1983 | Japan . |
| 58-121266 | 7/1983 | Japan . |
| 58-126839 | 7/1983 | Japan . |
| 59-80485 | 5/1984 | Japan . |
| 59-157057 | 9/1984 | Japan . |
| 60-13731 | 1/1985 | Japan . |
| 60-224666 | 11/1985 | Japan . |
| 786128 | 11/1957 | United Kingdom . |
| 2078727 | 1/1982 | United Kingdom . |
| 2121406 | 12/1983 | United Kingdom . |
| 2134110 | 8/1984 | United Kingdom . |

OTHER PUBLICATIONS

Koch, M. et al., Z. Naturforsch, B, Anorg. Chem. Drg., Chem vol. 37B(9), pp. 1201–1204, (1982).

Osman, M. A. et al., Mol. Cryst. Liq. Cryst., vol. 82, (Left), pp. 339–344 (1983).

Copy of Certified Translation of Swiss Patent Application CH–1900/84–8, (1984).

*Primary Examiner*—Philip Tucker
*Attorney, Agent, or Firm*—Millen, White, Zelano & Branigan

[57] ABSTRACT

Anisotropic compounds of the formula (1) specified in claim 1 are suitable, owing to their low $\Delta\epsilon/\epsilon\perp$ values for liquid crystal displays which have high information densities of for examples up to $10^6$ image dots and accordingly need to be highly multiplexible; compared with known compounds they offer improved application properties and are relatively simple to synthesize.

56 Claims, No Drawings

ANISOTROPIC COMPOUNDS AND LIQUID CRYSTAL MIXTURES THEREWITH

Matter enclosed in heavy brackets [ ] appears in the original patent but forms no part of this reissue specification; matter printed in italics indicates the additions made by reissue.

*This application is a continuation of application Ser. No. 07/444,251, filed Dec. 1, 1989 now abandoned, which in turn is a reissue of application Ser. No. 06/815,708, filed Dec. 16, 1985 (U.S. Pat. No. 4,710,315).*

BACKGROUND OF THE INVENTION

In electrooptical displays based on liquid crystals, which are also referred to as liquid crystal displays or LCDs, the liquid crystal phase is present as a dielectric between two sheetlike electrodes which are spaced from each other and are constructed in patterns or grids; selective excitation of predetermined electrode field regions has the effect of changing the position or orientation of the molecules of the dielectric within the regions of the selective excitation and thereby of bringing about a visible selective local modification of the dielectric.

This effect requires potentials whose size is dependent inter alia on the degree of anisotropy of the liquid crystal phase; this degree of anisotropy is expressed in general for a given liquid crystal substance by the difference ($\Delta$) of the dielectric constants ($\epsilon$) parallel to the electric field ($\epsilon\|$) minus that perpendicular thereto ($\epsilon\perp$), i.e. by the relationship referred to in short as dielectric constant anisotropy or DCA $\Delta\epsilon=\epsilon\|-\epsilon\perp$.

In liquid crystal displays which are based on the principle of the twisted nematic cell (TN=twisted nematic; see W. Helfrich, and M. Schadt, Appl. Phys. Lett. 18 (1971) 127), a property which is dependent upon the DCA is the so-called threshold voltage, which in turn must not be excessively high for various reasons, such as CMOS compatibility, and which in practice can be the smaller, the higher the value of $\Delta\epsilon$ is.

Since $\Delta\epsilon$ is the difference of two values, the same difference can be the result of very different pairs of values, for example the resulting DCA being the same for $$\Delta\epsilon=21(\epsilon\|)-20(\epsilon\perp)=1$$

$$\Delta\epsilon=2(\epsilon\|)-1(\epsilon\perp)=1.$$

For a completely different reason, namely because of the matrix addressing, which is essential in particular for displays having high information content (for example within the range of up to $10^6$ image dots per display), and the attendant desirability of a very steep and high shoulder of discontinuity in the voltage/contrast diagram of the liquid crystal dielectric of the liquid crystal display, the value of the ratio $\Delta\epsilon/\epsilon\perp$ should in addition be small; from the above numerical example it will be readily understood that this ideal can be approached in two ways, namely:

(a) by using appropriate liquid crystal mixtures of substances having a strongly positive or weakly negative DCA (see for example A. R. Kmetz, SID Digest, Tech. Papers IX (1078) 70); this has in particular the disadvantage that the mixtures tend to form smectic phases;

(b) by using substances which, in the molecule, have a marked polarization not only in the longitudinal direction but also in the transverse direction, relative to the generally "stretched" form of the liquid crystal molecules (M. A. Osman, European Patent Application Publication No. 0,019,665); this has the advantage that the ratio $\Delta\epsilon/\epsilon\perp$ can be reduced by increasing the contribution and not or not necessarily by reducing the $\epsilon\|$ contribution of the same molecule. The disadvantages of the compounds described in the citeed European patent application reside in their relatively high viscosity or relatively high melting points and in the usually difficult synthesis and/or low stability.

SUMMARY OF THE INVENTION

It is an object of the invention to specify a new class of anisotropic compounds which are suitable for liquid crystal displays or for liquid crystal mixtures and permit a substantially free choice of the $\Delta\epsilon$ and $\epsilon$ contributions by reducing or eliminating the disadvantages of the known compounds.

This object is achieved according to the invention with anisotropic compounds of the formula (1)

(I)

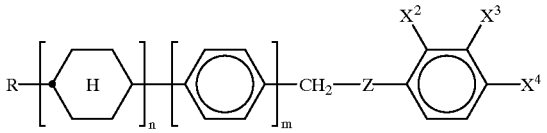

in which R is an alkyl, alkoxy, oxaalkyl, alkenyl or alkanoyloxy group which has in each case 1–12 C atoms in the alkyl moiety and which has a straight or branched and chiral or non-chiral chain, $X^2$ and $X^3$ are selected from hydrogen, halogen and nitrile, $X^4$ is halogen or nitrile, Z is the methylene group —$CH_2$— or the ether oxygen bridge —O— and m and n are each 0, 1 or 2 with the provisos that (a) the sum of n and m is at least 1 and at most 3, (b) m is 2 and n 0 if Z is —$CH_2$— and $X^4$ nitrile, (c) at least one of the groups $X^2$ and $X^3$ is not hydrogen and (d) n is 0 or 1 if Z is —$CH_2$— and $X^4$ halogen.

R is preferably an alkyl, alkoxy or alkanoyloxy group which has in each case 1–12 C atoms in the alkyl moiety and which has a straight or branched and chiral or non-chiral chain, i.e. $C_1$–$C_{12}$-alkyl, $C_1$–$C_{12}$-alkoxy and

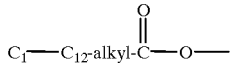

groups, such as, for example, methyl, ethyl, propyl, butyl, pentyl, hexyl, heptyl, octyl, nonyl, decyl, undecyl or dodecyl as alkyl moiety including the corresponding chiral-isomeric alkyl moieties such as, for example, 1-methylpropyl, 1-methylbutyl, 2-methylbutyl, 1-methylpentyl, 2-methylpentyl, 3-methylpentyl, 1- or 2- or 3- or 4-methylhexyl, 1- or 2- or 3- or 4- or 5-methylheptyl and further alkyl-alkyl groups formed on that basis and having an asymmetrical C atom. Alkyl moieties having 2–8 C atoms, in particular 3–8 C atoms, are frequently preferable.

In the formula (I), $X^2$ and $X^3$ are selected from hydrogen, halogen, fluorine, chlorine, bromine, iodine and nitrile (—C═N) with the proviso that at least one of the groups $X^2$ and $X^3$ is not hydrogen; Z is the methylene group —$CH_2$— or the ether oxygen bridge —O—; m and n are each 0, 1 or 2 with the proviso that the sum of n and m is at least 1 and at most 3. For many purposes preference is given to compounds (1) in which n is 1 or 2, preferably 1, and m is 0 or 1. Z is preferably the ether oxygen bridge —O—.

Preferably one of the groups $X^2$ and $X^3$ is fluorine and the other hydrogen.

$X^4$ is halogen or nitrile, preferably nitrile, fluorine or chlorine. If (m+n) is 2 or 3 and n is 1 or 2 and Z is —$CH_2$—, X is preferably F or Cl, particularly preferably F. If (m+n) is 1 and Z is —$CH_2$—, $X^4$ is preferably F or Cl, particularly preferably F.

A preferred group of compounds (1) thus has the formula (9)

(9)

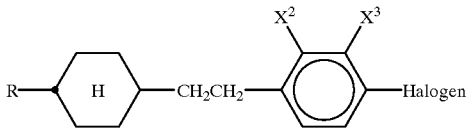

in which R, $X^2$ and $X^3$ have the abovementioned meaning and Halogen is fluorine or chlorine, preferably fluorine.

A preferred group of compounds (1) has the formula (2)

(2)

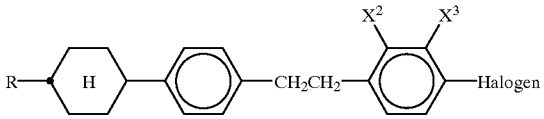

in which R, $X^2$ and $X^3$ have the abovementioned meaning and Halogen is preferably fluorine or chlorine, in particularly fluorine.

In a similarly preferred group of compounds of the formula (1) or (2), R is an alkyl group having 1–12 C atoms, preferably having 3–9 C atoms, such as, for example, n-pentyl or n-heptyl.

For many purposes, preference is further given to compounds (1) of the invention which have a longitudinally polarizing wing group, i.e. those in which $X^4$ is the nitrile group (—C≡N) or a halogen atom, in particular F, one of $X^2$, $X^3$ being a halogen atoms, in particular fluorine, and the other of $X^2$, $X^3$ being the hydrogen atom.

A further generally preferred group of compounds (1) are those of the formula (6)

(6)

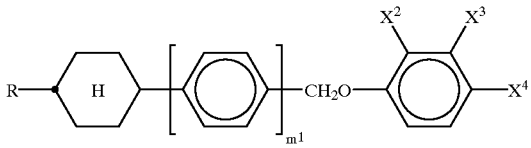

in which R, $X^2$, $X^3$ and $X^4$ have the general preferred meaning specified for the formula (1) and $m^1$ is 0 or 1.

A further generally preferred group of compounds (1) are those of the formula (7)

(7)

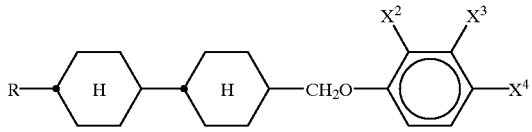

in which R, $X^2$, $X^3$ and $X^4$ have the meaning specified in claim 1 and $X^4$ is preferably CN, F or Cl, in particular preferably CN. A further generally preferred group of compounds (1) are those of the formula (8)

(8)

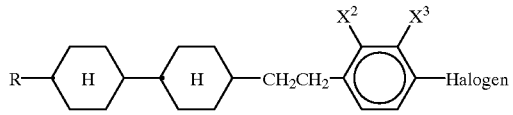

in which R, $X^2$ and $X^3$ have the meaning specified in claim 1.

R, $X^2$ and $X^3$ have the formulae (7) and (8) the general or preferred meaning specified for the formula (1).

The provision of compounds of the formula (1) also very generally represents an immense widening of the range of liquid crystal substances which, from various application aspects, are suitable for preparing nematic mixtures.

The compounds of the formula (1) have a wide range of uses. Depending on the choice of substituents, these compounds can be used as base materials of which liquid crystal dielectrics are predominantly composed; however, it is also possible to add to compounds of the formula (1) liquid crystal base materials from other classes of compound, for example in order to reduce the dielectric and/or optical anisotropy of such a dielectric. The compounds of formula (1) are also suitable as intermediates for preparing other substances which can be used as components of liquid crystal dielectrics.

The compounds of the formula (1) are in the pure state colourless and form liquid crystal mesophases within a temperature range which is favourably located for electro-optical use. They are very stable chemically, thermally and to light.

The invention thus relates to the compounds of the formula (1) and to the use of the compounds of the formula (1) as components of liquid crystal phases. The invention further relates to liquid crystal mixtures containing at least one compound of the formula (1) and liquid crystal display elements, in particular those with multiplex operation, which contain such mixtures.

Compounds of the formula (1) which have a branched wing group R can occasionally be of importance owing to superior solubility in the customary liquid crystal base materials, but in particular as chiral dopants, provided they are optically active. Branched groups of this kind generally contain not more than one chain branching. Preferred branched radicals R are isopropyl, 2-butyl (=1-methypropyl), isobutyl (2-methylpropyl), 2-methylbutyl, isopentyl (=3-methylbutyl), 2-methylpentyl, 3-methylpentyl, 2-ethylhexyl, 2-propylpentyl, 2-octyl, isopropoxy, 2-methylpropoxy, 2-methylbutoxy, 3-methylbutoxy, 2-methylpentoxy, 3-methylpentoxy, 2-ethylhexoxy, 1-methylhexoxy, 2-octyloxy, 2-oxa-3-methylbutyl and 3-oxa-4-methylpentyl. Such compounds can be used as components of smectic mixtures having ferroelectric properties.

Of the compounds of the formula (1), preference is given to those in which at least one of the radicals contained therein has one of the specified preferred meanings.

The compounds of the formula (1) are prepared by conventional methods, as described in the literature (for example in the standard works such as Houben-Weyl, Methoden der Organischen Chemie [Methods of Organic Chemistry], Georg Thieme-Verlag, Stuttgart), and in fact under reaction conditions which are known and suitable for the stated reactions using, if so desired, conventional variants which are not described here in detail.

The skilled person, through routine methods, can find appropriate methods of synthesis in the state of the art (for example German Offenlegungsschriften Nos. 2,344,732, 2,450,088, 2,429,093, 2,502,904, 2,636,684, 2,701,591 and 2,752,975 concerning compounds having 1,4-cyclohexylene and 1,4-phenylene groups; German Offenlegungsschrift No. 3,208,089, German Offenlegungsschrift No. 3,117,152, German Offenlegungsschrift No. 3,042,391 and European Offenlegungsschrift No. 84,194 concerning laterally substituted compounds; and German Offenlegungsschrift No. 3,201,721 concerning compounds having —$CH_2CH_2$— bridge members).

The starting materials can, if desired, also be formed in situ by not isolating them out of the reaction mixture but immediately reacting them further to give the compounds of the formula (1).

For instance, those compounds of the formula (1) in which Z is the methylene bridge (—$CH_2$—) can preferably be prepared for example in accordance with scheme I below using a Grignard reaction and subsequent reduction, while those compounds of the formula (1) in which Z is the ether oxygen bridge (—O—) are advantageously accessible by condensation as per scheme II. Compounds of the formula (1) in which $X^2$, $X^3$ or $X^4$ is the nitrile group can be obtained by nitrilation from the corresponding compounds (1) in which the corresponding $X^2$, $X^3$ or $X^4$ is a halogen atom suitable for nitrilation, for example bromine.

Schemes I and II are subject to the further definitions:

A is the radical

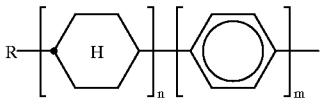

and

B is the radical

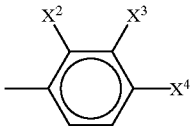

in which R, n, m, $X^2$, $X^3$ and $X^4$ have the abovementioned meaning.

SCHEME I

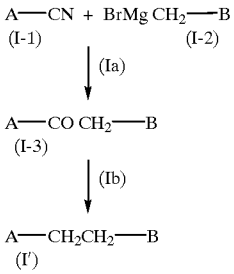

SCHEME II

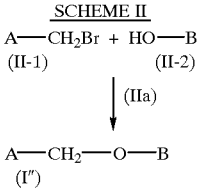

Suitable compounds of the formulae (I-1) and (I-2) and of the formulae (II-1) and (II-2) are either known or are obtainable analogously to the known compounds by standard methods.

An example of preparing a compound of the formula (I-2) is illustrated in scheme III below.

SCHEME III

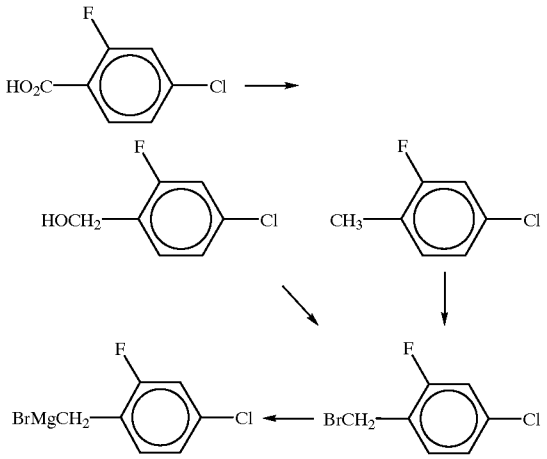

Liquid crystal mixtures (phases) according to the invention consist of 2 to 25, preferably 3 to 15, compoonents, including at least one compound of the formula (1). The other constituents are preferably selected from the nematic or nematogenic substances, in particular the known substances, from the classes of the azoxybenzenes, benzylideneanilines, biphenyls, terphenyls, phenyl or cyclohexyl benzoates, phenyl or cyclohexyl cyclohexanecarboxylate, phenylcyclohexanes, cyclohexylbiphenyls, cyclohexylcyclohexanes, cyclohexylnaphthalenes, 1,4-biscyclohexylbenzenes, 4,4'-biscyclohexylbiphenyls, phenyl- or cyclohexyl-pyrimidines, phenyl- or cyclohexyl-dioxanes, phenyl- or cyclohexyl-1,3-dithianes, 1,2-diphenylethanes, 1,2-dicyclohexylethanes, 1-cyclohexyl-2-phenylethanes, halogenated and non-halogenated stilbenes, benzyl phenyl ether, tolanes and substituted cinnamic acids.

The most important compounds which come into consideration as constituents of such liquid crystal phases can be characterized by the formula II $$R'—L—G—E—R'' \qquad II$$

in which L and E are each a carocyclic or heterocyclic ring system from the group comprising 1,4-disubstituted benzene and cyclohexane rings, 4'4-disubstituted biphenyl, phenylcyclohexane and cyclohexylcyclohexane systems, 2,5-disubstituted pyrimidine and 1,3-dioxane rings, 2,6-disubstituted naphthalene di- and tetrahydronaphthalene, quinazoline and tetrahydroquinazoline,

| | |
|---|---|
| —CH═CH— | —N(O)═N— |
| —CH═CY— | —CH═N(O)— |
| —CH≡C— | —$CH_2$—$CH_2$— |
| —CO—O— | —$CH_2$—O— |
| —CO—S— | —$CH_2$—S— |
| —CH═N— | —COO—Phe—COO— |

or a C—C single bond, Y is halogen, preferably chlorine or —CN, and R' and R" are alkyl, alkoxy, alkanoyloxy or alkoxycarbonyloxy having up to 18, preferably up to 8, carbon atoms, or one of these radicals can also be CN, NC, $NO_2$, $CF_3$, F, Cl or Br.

In most of these compounds, R' and R" are different from each other, one of these radicals usually being an alkyl or alkoxy group. But it is also possible to use other variants of the proposed substituents. Many such substances or mixtures thereof are commercially available. All these substances can be prepared by methods described in the literature.

The phases according to the invention contain about 0.1 to 100, preferably 10 to 100%, of one or more compounds of the formula I.

Preference is also given to dielectrics according to the invention which contain 0.1 to 40, preferably 0.5 to 30%, of one or more compounds of the formula I.

The dielectrics according to the invention are prepared in conventional manner. As a rule, the components are dissolved in one another, advantageously at elevated temperature.

By means of suitable additives it is possible to modify the liquid crystal dielectrics according to the invention in such a way that they can be used in any previously disclosed type of liquid display element.

Such additives are known to the skilled person and are described in the literature in detail. For example it is possible to add conducting salts, preferably ethyldimethyldodecylammonium 4-hexyloxybenzoate, tetrabutylammonium tetraphenylboronate or complex salts of crown ethers (cf. for example I. Haller et al., Mol. Cryst. Liq. Cryst. volume 24, pages 249–258 (1973)) for improving the conductivity, dichroic dyes for preparing coloured guest-host systems or substances for modifying the dielectric anisotropy, the viscosity and/or the orientation of the nematic phases. Such substances are described for example in German Offenlegungsschriften Nos. 2,209,127, 2,240,864, 2,321,632, 2,338,281, 2,450,088, 2,637,430, 2,853,728 and 2,902,177.

The following examples will illustrate the invention without limiting it. m.p.=melting point, c.p.=clear point. Here tofore and hereinafter percentages are by weight; all temperatures are in degrees Celsius. "Conventional working up" means: addition of water, extraction with methylene chloride, separation, drying of the organic phase, evaporation and clarification of the product by distillation, crystallization and/or chromatography.

EXAMPLE 1

Preparation of 4-(trans-4-pentylcyclohexylmethoxy)-3-fluorobenzonitrile; formula 6: R=n-pentyl, $m^1$=O, $X^2$=F, $X^4$=CN This compound was prepared in accordance with scheme IV below. To this end, butan-2-one (50 ml) was added to 4-hydroxy-3-fluorobenzonitrile (1.0 g, 0.0074 mole) and trans-4-pentylcyclohexylmethyl bromide (2.5 g, 0.0102 mole); the mixture was heated to the reflux temperature, was maintained at the reflux temperature for 48 hours with stirring, was then cooled down to room temperature and was poured into water (250 ml), and the mixture was extracted with chloroform (three times 50 ml). The combined organic phases were washed with water and dried over magnesium sulfate. The crude product obtained after the chloroform had been evaporated off was purified by column chromatography over silica gel using toluene as the eluent. After the toluene had been evaporated off, the product was repeatedly recrystallized from methanol until the phase transition temperatures (in degrees Celsius, K=crystalline; N=nematic,; I=isotropic) were constant; the corresponding values were: K.57.5.N(45.5).I.

The trans-4-pentylcyclohexylmethyl bromide used was obtained by the method described in European Patent Application No. 80201158.5 from the corresponding carboxylic acid by reduction to give the corresponding methanol derivative and bromination of the latter.

The 4-hydroxy-3-fluorobenzonitrile was prepared as follows:

4-Bromo-2-fluoroanisole was obtained in almost quantitative yield by the method described by Gray, G. W., and Jones, B. (J. Chem. Soc. (1954), (1967)) and was heated in an amount of 93 g (0.4537 mole) with anhydrous copper (I) cyanide (49 g, 0.0544 mole) in dry dimethylformamide (90 ml) under reflux for 3.5 hours by the method described by Adamska, G. et al. (Mol. Cryst. Liqu. Cryst. 76 (1981) 93). The crude product thus obtained gave 39 g (57% yield) of pure 4-methoxy-3-fluorobenzonitrile, m.p. 98.5° to 99° C.

5.0 g (0.0329 mole) of the compound thus obtained and 8.75 g (0.0658 mole) of anhydrous aluminium chloride were used together with 1.9 g (0.0329 mole) of sodium chloride to prepare a finely pulverulent mixture which was heated under anhydrous conditions at 210° C. on an oil bath for 40 min. After cooling down, the mixture was treated with 250 ml of water and was extracted three times with 50 ml of diethyl ether each time. The combined ether extracts were extracted with sodium chloride solution (2×250 ml) and dried over magnesium sulfate. The solvent was evaporated under slightly reduced pressure, and the residue was crystallized from 1:1 toluene:hexane. This gave 3.0 g (66% yield) of pure 4-hydroxy-3-fluorobenzonitrile, m.p. 133.5° to 134.5° C.

SCHEME IV

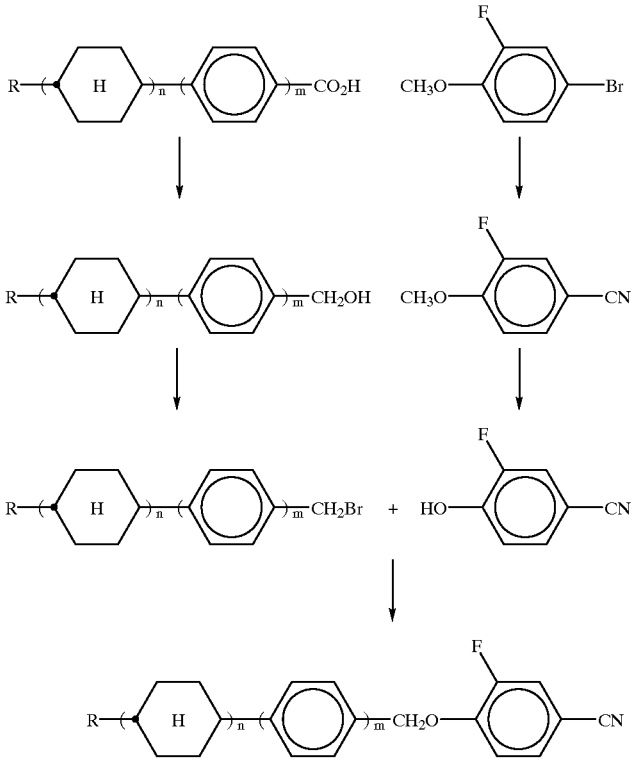

Analogously to scheme IV 4-hydroxy-2-fluorobenzonitrile can be used to produce the corresponding isomeric compounds according to the invention.

EXAMPLES 2–4

The method described in Example 1 was used to prepare compounds according to the invention of the formulae (20), (30), (40) and (50) indicated hereinafter and of the similarly indicated phase transition temperatures:

(20)

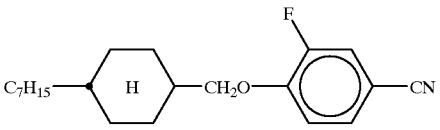

K 69.5.N (51).I (30)

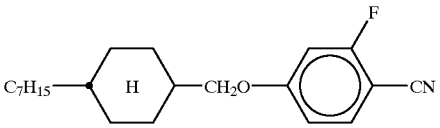

K 37.N (24.5).I (40)

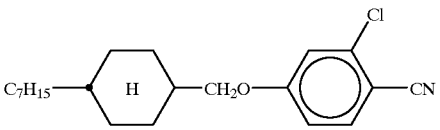

K 39.N (-30).I

-continued (50)

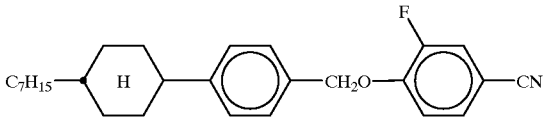

K 72.5.SS 73.5.N 85.I

EXAMPLES 5–6

The method depicted in scheme V below was used to prepare the compounds according to the invention.

2-(4-[trans-4-heptylcyclohexyl]phenyl)-1-(4-chloro-2-fluorophenyl)ethane (K.58.5.N.83.I)

and 2-(4-[trans-4-pentylcyclohexyl]phenyl)-1-(4-chloro-2-fluorophenyl)ethane.

SCHEME V

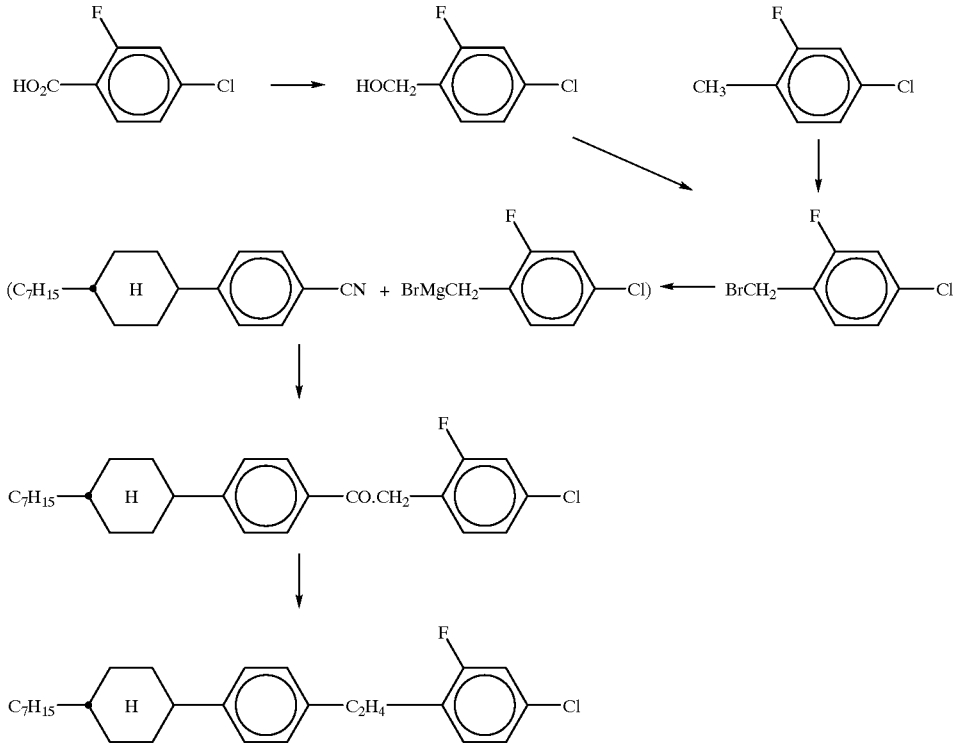

Further examples of compounds according to the invention of the formula (1) are as follows:

2-(4-trans-methylcyclohexyl)-1-(4-chloro-2-fluorophenyl) ethane
2-(4-trans-ethylcyclohexyl)-1-(4-chloro-2-fluorophenyl) ethane
2-(4-trans-propylcyclohexyl)-1-(4-chloro-2-fluorophenyl) ethane
2-(4-trans-butylcyclohexyl)-1-(4-chloro-2-fluorophenyl) ethane
2-(4-trans-pentylcyclohexyl)-1-(4-chloro-2-fluorophenyl) ethane
2-(4-trans-hexylcyclohexyl)-1-(4-chloro-2-fluorophenyl) ethane
2-(4-trans-heptylcyclohexyl)-1-(4-chloro-2-fluorophenyl) ethane
2-(4-trans-octylcyclohexyl)-1-(4-chloro-2-fluorophenyl) ethane
2-(4-trans-methylcyclohexyl)-1-(4-chloro-3-fluorophenyl) ethane
2-(4-trans-ethylcyclohexyl)-1-(4-chloro-3-fluorophenyl) ethane
2-(4-trans-propylcyclohexyl)-1-(4-chloro-3-fluorophenyl) ethane
2-(4-trans-butylcyclohexyl)-1-(4-chloro-3-fluorophenyl) ethane
2-(4-trans-pentylcyclohexyl)-1-(4-chloro-3-fluorophenyl) ethane
2-(4-trans-hexylcyclohexyl)-1-(4-chloro-3-fluorophenyl) ethane
2-(4-trans-heptylcyclohexyl)-1-(4-chloro-3-fluorophenyl) ethane
2-(4-trans-octylcyclohexyl)-1-(4-chloro-3-fluorophenyl) ethane
2-(4-trans-methylcyclohexyl)-1-(2,4-difluorophenyl)ethane
2-(4-trans-ethylcyclohexyl)-1-(2,4-difluorophenyl)ethane
2-(4-trans-propyllcyclohexyl)-1-(2,4-difluorophenyl)ethane
2-(4-trans-butylcyclohexyl)-1-(2,4-difluorophenyl)ethane
2-(4-trans-pentylcyclohexyl)-1-(2,4-difluorophenyl)ethane
2-(4-trans-hexylcyclohexyl)-1-(2,4-difluorophenyl)ethane
2-(4-trans-heptylcyclohexyl)-1-(2,4-difluorophenyl)ethane
2-(4-trans-methylcyclohexyl)-1-(3,4-difluorophenyl)ethane
2-(4-trans-ethylcyclohexyl)-1-(3,4-difluorophenyl)ethane
2-(4-trans-propylcyclohexyl)-1-(3,4-difluorophenyl)ethane
2-(4-trans-butylcyclohexyl)-1-(3,4-difluorophenyl)ethane
2-(4-trans-pentylcyclohexyl)-1-(3,4-difluorophenyl)ethane
2-(4-trans-hexylcyclohexyl)-1-(3,4-difluorophenyl)ethane
2-(4-trans-heptylcyclohexyl)-1-(3,4-difluorophenyl)ethane
2-(4-trans-4-propyl-4'-bicyclohexyl)-1-(4-chloro-2-fluorophenyl)ethane
2-(4-trans-4-pentyl-4'-bicyclohexyl)-1-(4-chloro-2-fluorophenyl)ethane
2-(4-trans-4-heptyl-4'-bicyclohexyl)-1-(4-chloro-2-fluorophenyl)ethane
2-(4-trans-4-propyl-4'-bicyclohexyl)-1-(4-chloro-3-fluorophenyl)ethane
2-(4-trans-4-pentyl-4'-bicyclohexyl)-1-(4-chloro-3-fluorophenyl)ethane
2-(4-trans-4-heptyl-4'-bicyclohexyl)-1-(4-chloro-3-fluorophenyl)ethane
2-(trans-4-methyl-4'-bicyclohexyl)-1-(2,4-difluorophenyl) ethane
2-(trans-4-ethyl-4'-bicyclohexyl)-1-(2,4-difluorophenyl) ethane
2-(trans-4-propyl-4'-bicyclohexyl)-1-(2,4-difluorophenyl) ethane
2-(trans-4-butyl-4'-bicyclohexyl)-1-(2,4-difluorophenyl) ethane 2-(trans-4-pentyl-4'-bicyclohexyl)-1-(2,4-difluorophenyl) ethane
2-(trans-4-hexyl-4'-bicyclohexyl)-1-(2,4-difluorophenyl) ethane
2-(trans-4-heptyl-4'-bicyclohexyl)-1-(2,4-difluorophenyl) ethane
2-(trans-4-methyl-4'-bicyclohexyl)-1-(3,4-difluorophenyl) ethane
2-(trans-4-ethyl-4'-bicyclohexyl)-1-(3,4-difluorophenyl) ethane
2-(trans-4-propyl-4'-bicyclohexyl)-1-(3,4-difluorophenyl) ethane
2-(trans-4-butyl-4'-bicyclohexyl)-1-(3,4-difluorophenyl) ethane
2-(trans-4-pentyl-4'-bicyclohexyl)-1-(3,4-difluorophenyl) ethane
2-(trans-4-hexyl-4'-bicyclohexyl)-1-(3,4-difluorophenyl) ethane
2-(trans-4-heptyl-4'-bicyclohexyl)-1-(3,4-difluorophenyl) ethane
2-(4'-methylbiphenyl-4-yl)-1-(4-cyano-3-fluorophenyl) ethane
2-(4'-ethylbiphenyl-4-yl)-1-(4-cyano-3-fluorophenyl)ethane
2-(4'-propylbiphenyl-4-yl)-1-(4-cyano-3-fluorophenyl) ethane
2-(4'-butylbiphenyl-4-yl)-1-(4-cyano-3-fluorophenyl)ethane
2-(4'-pentylbiphenyl-4-yl)-1-(4-cyano-3-fluorophenyl) ethane
2-(4'-hexylbiphenyl-4-yl)-1-(4-cyano-3-fluorophenyl) ethane
2-(4'-heptylbiphenyl-4-yl)-1-(4-cyano-3-fluorophenyl) ethane
2-(4'-methoxybiphenyl-4-yl)-1-(4-cyano-3-fluorophenyl) ethane
2-(4'-ethoxybiphenyl-4-yl)-1-(4-cyano-3-fluorophenyl) ethane
2-(4'-proproxybiphenyl-4-yl)-1-(4-cyano-3-fluorophenyl) ethane
2-(4'-butoxybiphenyl-4-yl)-1-(4-cyano-3-fluorophenyl) ethane
2-(4'-pentoxybiphenyl-4-yl)-1-(4-cyano-3-fluorophenyl) ethane
4-(trans-4-propylcyclohexylmethoxy)-3-fluorobenzonitrile
4-(trans-4butylcyclohexylmethoxy)-3-fluorobenzonitrile
4-(trans-4-pentylcyclohexylmethoxy)-3-fluorobenzonitrile
4-(trans-4-ethylcyclohexylmethoxy)-3-fluorobenzonitrile
4-(trans-4-hexylcyclohexylmethoxy)-3-fluorobenzonitrile
4-(trans-4-octylcyclohexylmethoxy)-3-fluorobenzonitrile
4-(trans-4-methylcyclohexylmethoxy)-3-chlorobenzonitrile
4-(trans-4-ethylcyclohexylmethoxy)-3-chlorobenzonitrile
4-(trans-4-propylcyclohexylmethoxy)-3-chlorobenzonitrile
4-(trans-4-butylcyclohexylmethoxy)-3-chlorobenzonitrile
4-(trans-4-pentylcyclohexylmethoxy)-3-chlorobenzonitrile
4-(trans-4-hexylcyclohexylmethoxy)-3-chlorobenzonitrile
4-(trans-4-heptylcyclohexylmethoxy)-3-chlorobenzonitrile
4-(trans-4-propylcyclohexylmethoxy)-2-fluorobenzonitrile
4-(trans-4-butylcyclohexylmethoxy)-2-fluorobenzonitrile
4-(trans-4-pentylcyclohexylmethoxy)-2-fluorobenzonitrile
4-(trans-4-hexylcyclohexylmethoxy)-2-fluorobenzonitrile
4-(trans-4-heptylcyclohexylmethoxy)-2-fluorobenzonitrile
4-(trans-4-octylcyclohexylmethoxy)-2-fluorobenzonitrile
4-cyano-2-fluorophenyl 4-(trans-4-propylcyclohexyl)benzyl ether
4-cyano-2-fluorophenyl 4-(trans-4-pentylcyclohexyl)benzyl ether
4-cyano-3-fluorophenyl 4-(trans-4-propylcyclohexyl)benzyl ether
4-cyano-3-fluorophenyl 4-(trans-4-pentylcyclohexyl)benzyl ether
4-cyano-3-fluorophenyl 4-(trans-4-heptylcyclohexyl)benzyl ether
4-(trans-4-propyl-4'-bicyclohexylmethoxy)-3-fluorobenzonitrile
4-(trans-4-pentyl-4'-bicyclohexylmethoxy)-3-fluorobenzonitrile
4-(trans-4-heptyl-4'-bicyclohexylmethoxy)-3-fluorobenzonitrile
4-(trans-4-propyl-4'-bicyclohexylmethoxy)-2-fluorobenzonitrile
4-(trans-4-pentyl-4'-bicyclohexylmethoxy)-2-fluorobenzonitrile
4-(trans-4-heptyl-4'-bicyclohexylmethoxy)-2-fluorobenzonitrile
4-(trans-4-propyl-4'-bicyclohexylmethoxy)-1,2-benzodicarbonitrile
4-(trans-4-pentyl-4'-bicyclohexylmethoxy)-1,2-benzodicarbonitrile
4-(trans-4-heptyl-4'-bicyclohexylmethoxy)-1,2-benzodicarbonitrile
4-(trans-4-propyl-4'-bicyclohexylmethoxy)-1,3-benzodicarbonitrile
4-(trans-4-pentyl-4'-bicyclohexylmethoxy)-1,3-benzodicarbonitrile
4-(trans-4-heptyl-4'-bicyclohexylmethoxy-1,3-benzodicarbonitrile Liquid crystal mixtures according to the invention contain at least one compound of the formula (1), usually together with known liquid crystal substances and additives which are known for the operation of electro-optical display cells of the various types. Preferably such mixtures contain two or more different compounds of the formula (1), for example in total in amounts of 1–90 mole %; such mixtures can be obtained in conventional manner by combining the components, if appropriate heating and mixing and can be introduced in known manner into the display cells.

Liquid crystal compounds according to the invention of the formula (1) are of particular advantage, in particular for base mixtures which are generally suitable for twisted nematic cells which each require a high degree of multiplexibility in order to offer high information densities, for example for input or/and output facilities in portable systems, for example for text editors, teletext equipment, personal computers, memory oscilloscopes and the like.

We claim:

1. A compound of the formula

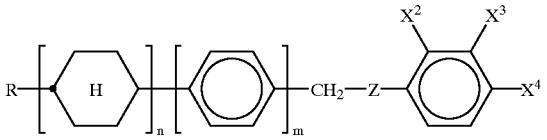

in which R is an alkyl, alkoxy, or alkanoyloxy group which has in each case 1–12 C atoms in the alkyl moiety and which has a straight or branched and chiral or non-chiral chain, $X^2$ and $X^3$ are independently hydrogen, halogen or nitrile, $X^4$ is halogen or nitrile, Z is the ether oxygen bridge —O— and m and n are independently 0, 1 or 2 with the provisos that (a) the sum of n and m is at least 1 and at most 3, and (b) at least one of the groups $X^2$ and $X^3$ is not hydrogen.

2. A compound according to claim 1, wherein R is an alkyl group having 1–12 C atoms.

3. A compound according to claim 1 or 2, wherein halogen is fluorine or chlorine.

4. A compound according to claim 1, wherein one of $X^2$, $X^3$ is a halogen atom and the other is hydrogen.

5. A compound according to claim 1, of the formula (6)

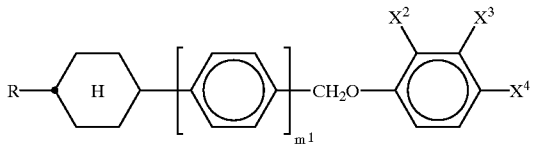

in which R, $X^2$, $X^3$ and $X^4$ have the meaning specified in claim 1 and $m^1$ if 0 or 1.

6. A compound according to claim 5, wherein R is an alkyl group having 1–12 C atoms.

7. A compound according to claim 5 or 6, wherein $X^4$ is a nitrile group and one of $X^2$, $X^3$ is a halogen atom and the other is hydrogen.

8. A compound according to claim 5 or 6, wherein $X^2$ is fluorine.

9. A compound according to claim 6 [or 7,] wherein $X^3$ is fluorine or chlorine.

10. A compound according to claim 1, of the formula (7)

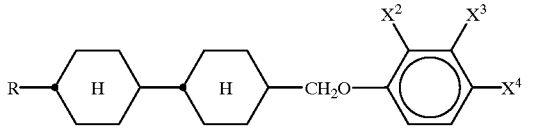

in which R, $X^2$, and $X^3$ and $X^4$ have the meaning specified in claim 1.

11. A compound according to claim 10, wherein R is an alkyl group having 1–12 C atoms.

12. A compound according to claim 10 or 11, wherein $X^4$ is a nitrile group and one of $X^2$, $X^3$ is a halogen atom and the other is hydrogen.

13. A compound according to claim 10 or 11 wherein $X^2$ is fluorine.

14. A compound according to claim 10 or 11 wherein $X^3$ is fluorine or chlorine.

15. In a liquid crystal mixture having at least two liquid crystal components; the improvement wherein at least one such component is a compound of claim 1.

16. In an electro-optical display element with multiplex operation comprising a liquid crystal mixture as dielectric, the improvement wherein the mixture is one of claim 15.

*17. A compound of the formula (8)*

*(8)*

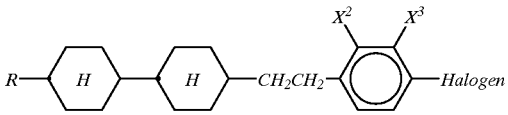

*wherein*

*R is an alkyl, alkoxy, alkenyl or alkanoyloxy group which has in each case 1–12 C atoms in the alkyl moiety and which has a straight or branched and chiral or non-chiral chain,*

*$X^2$ and $X^3$ are independently hydrogen, halogen or nitrile, and*

*Halogen is fluorine or chlorine,*

*with the proviso that at least one of the groups $X^2$ and $X^3$ is not hydrogen.*

*18. A compound of claim 17, wherein R is alkyl of 1–12 C atoms.*

*19. A compound of claim 17, wherein $X^2$ and $X^3$ are H, F or Cl.*

*20. A compound of claim 17, wherein one of $X^2$ and $X^3$ is F and the other is H.*

*21. A compound of claim 17, wherein $X^2$ is H, $X^3$ is F and Halogen is F.*

*22. A compound of claim 20, wherein halogen is Cl.*

*23. A compound of claim 17 which is*

*2-(4-trans-4-propyl-4'-bicyclohexyl)-1-(4-chloro-2-fluorophenyl)ethane*

*2-(4-trans-4-pentyl-4'-bicyclohexyl)-1-(4-chloro-2-fluorophenyl)ethane*

*2-(4-trans-4-heptyl-4'-bicyclohexyl)-1-(4-chloro-2-fluorophenyl)ethane*

*2-(4-trans-4-propyl-4'-bicyclohexyl)-1-(4-chloro-3-fluorophenyl)ethane*

*2-(4-trans-4-pentyl-4'-bicyclohexyl)-1-(4-chloro-3-fluorophenyl)ethane*

*2-(4-trans-4-heptyl-4'-bicyclohexyl)-1-(4-chloro-3-fluorophenyl)ethane*

*2-(trans-4-methyl-4'-bicyclohexyl)-1-(2,4-difluorophenyl)ethane*

*2-(trans-4-ethyl-4'-bicyclohexyl)-1-(2,4-difluorophenyl) ethane*

*2-(trans-4-propyl-4'-bicyclohexyl)-1-(2,4-difluorophenyl) ethane*

*2-(trans-4-butyl-4'-bicyclohexyl)-1-(2,4-difluorophenyl) ethane*

*2-(trans-4-pentyl-4'-bicyclohexyl)-1-(2,4-difluorophenyl) ethane*

*2-(trans-4-hexyl-4'-bicyclohexyl)-1-(2,4-difluorophenyl) ethane*

*2-(trans-4-heptyl-4'-bicyclohexyl)-1-(2,4-difluorophenyl) ethane*

*2-(trans-4-methyl-4'-bicyclohexyl)-1-(3,4-difluorophenyl)ethane*

*2-(trans-4-ethyl-4'-bicyclohexyl)-1-(3,4-difluorophenyl) ethane*

*2-(trans-4-propyl-4'-bicyclohexyl)-1-(3,4-difluorophenyl) ethane*

*2-(trans-4-butyl-4'-bicyclohexyl)-1-(3,4-difluorophenyl) ethane*

*2-(trans-4-pentyl-4'-bicyclohexyl)-1-(3,4-difluorophenyl) ethane*

*2-(trans-4-hexyl-4'-bicyclohexyl)-1-(3,4-difluorophenyl) ethane, or*

*2-(trans-4-heptyl-4'-bicyclohexyl)-1-(3,4-difluorophenyl) ethane.*

24. A compound of formula (9)

(9)

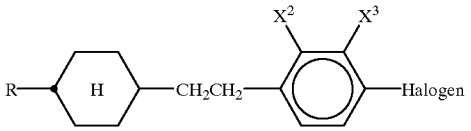

wherein

R is an alkyl, alkoxy, alkenyl or alkanoyloxy group which has in each case 1–12 C atoms in the alkyl moiety and which has a straight or branched and chiral or non-chiral chain, $X^2$ and $X^3$ are independently hydrogen, halogen or nitrile, and Halogen is fluorine or chlorine, with the proviso that at least one of the groups $X^2$ and $X^3$ is not hydrogen.

25. A compound of claim 24, wherein R is alkyl of 1–12 C atoms.

26. A compound of claim 24, wherein $X^2$ and $X^3$ are H, F or Cl.

27. A compound of claim 24, wherein one of $X^2$ and $X^3$ is F and the other is H.

28. A compound of claim 24, wherein $X^2$ is H, $X^3$ is F and Halogen is F.

29. A compound of claim 27, wherein halogen is Cl.

30. A compound of claim 24, which is 2-(4-trans-methylcyclohexyl)-1-(4-chloro-2-fluorophenyl)ethane 2-(4-trans-ethylcyclohexyl)-1-(4-chloro-2-fluorophenyl) ethane 2-(4-trans-propylcyclohexyl)-1-(4-chloro-2-fluorophenyl) ethane 2-(4-trans-butylcyclohexyl)-1-(4-chloro-2-fluorophenyl) ethane 2-(4-trans-pentylcyclohexyl)-1-(4-chloro-2-fluorophenyl) ethane 2-(4-trans-hexylcyclohexyl)-1-(4-chloro-2-fluorophenyl) ethane 2-(4-trans-heptylcyclohexyl)-1-(4-chloro-2-fluorophenyl) ethane 2-(4-trans-octylcyclohexyl)-1-(4-chloro-2-fluorophenyl) ethane 2-(4-trans-methylcyclohexyl)-1-(4-chloro-3-fluorophenyl)ethane 2-(4-trans-ethylcyclohexyl)-1-(4-chloro-3-fluorophenyl) ethane 2-(4-trans-propylcyclohexyl)-1-(4-chloro-3-fluorophenyl) ethane 2-(4-trans-butylcyclohexyl)-1-(4-chloro-3-fluorophenyl) ethane 2-(4-trans-pentylcyclohexyl)-1-(4-chloro-3-fluorophenyl) ethane 2-(4-trans-hexylcyclohexyl)-1-(4-chloro-3-fluorophenyl) ethane 2-(4-trans-heptylcyclohexyl)-1-(4-chloro-3-fluorophenyl) ethane 2-(4-trans-octylcyclohexyl)-1-(4-chloro-3-fluorophenyl) ethane 2-(4-trans-methylcyclohexyl)-1-(2,4-difluorophenyl) ethane 2-(4-trans-ethylcyclohexyl)-1-(2,4-difluorophenyl)ethane 2-(4-trans-propylcyclohexyl)-1-(2,4-difluorophenyl) ethane 2-(4-trans-butylcyclohexyl)-1-(2,4-difluorophenyl)ethane 2-(4-trans-pentylcyclohexyl)-1-(2,4-difluorophenyl)ethane 2-(4-trans-hexylcyclohexyl)-1-(2,4-difluorophenyl)ethane 2-(4-trans-heptylcyclohexyl)-1-(2,4-difluorophenyl) ethane 2-(4-trans-methylcyclohexyl)-1-(3,4-difluorophenyl) ethane 2-(4-trans-ethylcyclohexyl)-1-(3,4-difluorophenyl)ethane 2-(4-trans-propylcyclohexyl)-1-(3,4-difluorophenyl) ethane 2-(4-trans-butylcyclohexyl)-1-(3,4-difluorophenyl)ethane 2-(4-trans-pentylcyclohexyl)-1-(3,4-difluorophenyl) ethane 2-(4-trans-hexylcyclohexyl)-1-(3,4-difluorophenyl) ethane, or 2-(4-trans-heptylcyclohexyl)-1-(3,4-difluorophenyl) ethane.

31. A compound of formula (2)

(2)

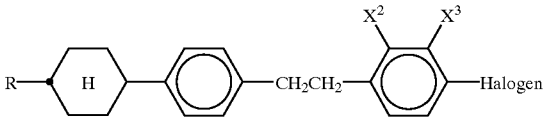

wherein

R is an alkyl, alkoxy, alkenyl or alkanoyloxy group which has in each case 1–12 C atoms in the alkyl moiety and which has a straight or branched and chiral or non-chiral chain, $X^2$ and $X^3$ are independently hydrogen, halogen or nitrile, and Halogen is fluorine or chlorine, with the proviso that at least one of the groups $X^2$ and $X^3$ is not hydrogen.

32. A compound of claim 31, wherein $X^2$ and $X^3$ are H, F or Cl.

33. A compound of claim 31, wherein one of $X^2$ and $X^3$ is F and the other is H.

34. A compound of claim 31, which is 2-(4-[trans-4-heptylcyclohexyl]phenyl)-1-(4-chloro-2-fluorophenyl)ethane, or 2-(4-[trans-4-pentylcyclohexyl]phenyl)-1-(4-chloro-2-fluorophenyl)ethane.

35. In a liquid crystal mixture having at least two liquid crystal components, the improvement wherein at least one such component is a compound of claim 17.

36. In a liquid crystal mixture having at least two liquid crystal components, the improvement wherein at least one such component is a compound of claim 24.

37. In a liquid crystal mixture having at least two liquid crystal components, the improvement wherein at least one such component is a compound of claim 31.

38. A compound of claim 31, wherein R is alkyl of 1–11 C atoms.

39. A compound of claim 31, wherein R is alkoxy or alkanoyloxy of 1–12 C atoms.

40. A compound of claim 31, wherein R is alkoxy, alkenyl or alkanoyloxy of 1–12 C atoms.

41. A compound of claim 31, wherein halogen is fluorine.

*42. A compound of claim 31, wherein halogen is chlorine.*

*43. A compound of claim 17, wherein R is alkyl of 1–11 C atoms.*

*44. A compound of claim 17, wherein R is alkoxy or alkanoyloxy of 1–12 C atoms.*

*45. A compound of claim 17, wherein R is alkoxy, alkenyl or alkanoyloxy of 1–12 C atoms.*

*46. A compound of claim 17, wherein R is alkyl, alkoxy or alkanoyloxy which has 1–12 C atoms in each case in the alkyl moiety.*

*47. A compound of claim 24, wherein R is alkyl, alkoxy or alkanoyloxy which has 1–12 C atoms in each case in the alkyl moiety.*

*48. A compound of claim 31, wherein R is alkyl, alkoxy or alkanoyloxy which has 1–12 C atoms in each case in the alkyl moiety.*

*49. A compound of claim 17, wherein R is alkenyl which has 1–12 C atoms in each case in the alkyl moiety.*

*50. A compound of claim 24, wherein R is alkenyl which has 1–12 C atoms in each case in the alkyl moiety.*

*51. A compound of claim 31, wherein R is alkenyl which has 1–12 C atoms in each case in the alkyl moiety.*

*52. A compound of claim 21, wherein R is alkyl.*

*53. A compound of claim 52 which is*

*2-(trans-4-methyl-4'-bicyclohexyl)-1-(2,4-difluorophenyl)-ethane*

*2-(trans-4-ethyl-4'-bicyclohexyl)-1-(2,4-difluorophenyl)-ethane*

*2-(trans-4-propyl-4'-bicyclohexyl)-1-(2,4-difluorophenyl)-ethane*

*2-(trans-4-butyl-4'-bicyclohexyl)-1-(2,4-difluorophenyl)-ethane*

*2-(trans-4-pentyl-4'-bicyclohexyl)-1-(2,4-difluorophenyl)-ethane*

*2-(trans-4-hexyl-4'-bicyclohexyl)-1-(2,4-difluorophenyl)-ethane*

*2-(trans-4-heptyl-4'-bicyclohexyl)-1-(2,4-difluorophenyl)-ethane*

*2-(trans-4-methyl-4'-bicyclohexyl)-1-(3,4-difluorophenyl)-ethane*

*2-(trans-4-ethyl-4'-bicyclohexyl)-1-(3,4-difluorophenyl)-ethane*

*2-(trans-4-propyl-4'-bicyclohexyl)-1-(3,4-difluorophenyl)-ethane*

*2-(trans-4-butyl-4'-bicyclohexyl)-1-(3,4-difluorophenyl)-ethane*

*2-(trans-4-pentyl-4'-bicyclohexyl)-1-(3,4-difluorophenyl)-ethane*

*2-(trans-4-hexyl-4'-bicyclohexyl)-1-(3,4-difluorophenyl)-ethane, or*

*2-(trans-4-heptyl-4'-bicyclohexyl)-1-(3,4-difluorophenyl)-ethane.*

*54. A compound of claim 28, wherein R is alkyl.*

*55. A compound of claim 54 which is*

*2-(4-trans-methylcyclohexyl)-1-(2,4-difluorophenyl)-ethane*

*2-(4-trans-ethylcyclohexyl)-1-(2,4-difluorophenyl)-ethane*

*2-(4-trans-propylcyclohexyl)-1-(2,4-difluorophenyl)-ethane*

*2-(4-trans-butylcyclohexyl)-1-(2,4-difluorophenyl)-ethane*

*2-(4-trans-pentylcyclohexyl)-1-(2,4-difluorophenyl)-ethane*

*2-(4-trans-hexylcyclohexyl)-1-(2,4-difluorophenyl)-ethane*

*2-(4-trans-heptylcyclohexyl)-1-(2,4-difluorophenyl)-ethane*

*2-(4-trans-methylcyclohexyl)-1-(3,4-difluorophenyl)-ethane*

*2-(4-trans-ethylcyclohexyl)-1-(3,4-difluorophenyl)-ethane*

*2-(4-trans-propylcyclohexyl)-1-(3,4-difluorophenyl)-ethane*

*2-(4-trans-butylcyclohexyl)-1-(3,4-difluorophenyl)-ethane*

*2-(4-trans-pentylcyclohexyl)-1-(3,4-difluorophenyl)-ethane*

*2-(4-trans-hexylcyclohexyl)-1-(3,4-difluorophenyl)-ethane, or*

*2-(4-trans-heptylcyclohexyl)-1-(3,4-difluorophenyl)-ethane.*

*56. A compound according to claim 7, wherein $X^3$ is fluorine or chlorine.*

* * * * *